(12) United States Patent
Jónsson et al.

(10) Patent No.: US 8,317,875 B2
(45) Date of Patent: Nov. 27, 2012

(54) NOISE REDUCTION DEVICE FOR ARTICULATING JOINT, AND A LIMB SUPPORT DEVICE HAVING THE SAME

(75) Inventors: Vilhjalmur Freyr Jónsson, Reykjavik (IS); Grímur Jónsson, Vogar (IS); Arinbjörn Clausen, Reykjavik (IS)

(73) Assignee: Össur hf, Reykjavik (IS)

( * ) Notice: Subject to any disclaimer, the term of this patent is extended or adjusted under 35 U.S.C. 154(b) by 422 days.

(21) Appl. No.: 12/638,672

(22) Filed: Dec. 15, 2009

(65) Prior Publication Data

US 2010/0152865 A1 Jun. 17, 2010

Related U.S. Application Data

(60) Provisional application No. 61/122,667, filed on Dec. 15, 2008.

(51) Int. Cl.
*A61F 2/66* (2006.01)
*F16C 11/04* (2006.01)

(52) U.S. Cl. ............... 623/52; 403/149; 623/47

(58) Field of Classification Search ................ 403/145, 403/148, 149; 623/47, 50, 52
See application file for complete search history.

(56) References Cited

U.S. PATENT DOCUMENTS

| 80,702 | A | | 8/1868 | Barr |
|---|---|---|---|---|
| 1,378,783 | A | * | 5/1921 | Griffeth .................... 403/149 |
| 1,755,852 | A | * | 4/1930 | Wagner .................... 403/148 |
| 1,778,452 | A | | 10/1930 | Ernst |
| 2,400,032 | A | | 5/1946 | Talbot |
| 2,652,292 | A | | 9/1953 | Sabee |
| 2,734,223 | A | | 2/1956 | Park |
| 2,987,349 | A | | 6/1961 | Kretzmer, Jr. |
| 3,033,622 | A | | 5/1962 | Renner |
| 3,122,399 | A | | 2/1964 | Hunter |
| 3,929,392 | A | | 12/1975 | Ogino |
| 4,704,099 | A | | 11/1987 | Rohloff |
| 5,258,038 | A | | 11/1993 | Robinson et al. |
| 5,800,567 | A | | 9/1998 | Cooper et al. |
| 6,206,933 | B1 | | 3/2001 | Shorter et al. |
| 6,469,411 | B2 | | 10/2002 | Lembke |
| 7,182,590 | B2 | | 2/2007 | Nishimura et al. |

FOREIGN PATENT DOCUMENTS

KR 2005-0022697 3/2005

OTHER PUBLICATIONS

International Search Report, PCT/US2009/068124, Mar. 5, 2010.

\* cited by examiner

*Primary Examiner* — David H. Willse
(74) *Attorney, Agent, or Firm* — Knobbe, Martens, Olson & Bear, LLP

(57) ABSTRACT

An articulating connection or joint for a limb support device having a first support member and a second support member pivotably couples together the first support member and the second support member. The articulating connection can include one or more first articulating connection member, or load-bearing pin, and one or more second articulating connection member, or bushing, disposed about the first and second support members. The load-bearing pin is coupled to one of the support members and the bushing is coupled to another of the support members. The bushing is configured to rotatingly receive the load-bearing pin and interacts with an actuation member configured to apply a force on the load-bearing pin to eccentrically align the load-bearing pin relative to the bushing so that the load-bearing pin continuously follows and contacts a bearing surface of the bushing during use of the limb support device, thereby inhibiting noise generation from the interaction of the bushing and load-bearing pin.

15 Claims, 10 Drawing Sheets

NOISE REDUCTION DEVICE FOR ARTICULATING JOINT, AND A LIMB SUPPORT DEVICE HAVING THE SAME

RELATED APPLICATION

This application claims the benefit of priority under 35 U.S.C. §119(e) of U.S. Provisional Application No. 61/122,667, filed on Dec. 15, 2008, and entitled "NOISE REDUCTION DEVICE FOR ARTICULATING JOINT, AND A LIMB SUPPORT DEVICE HAVING THE SAME," the entirety of which is hereby incorporated herein by reference and should be considered a part of this specification.

BACKGROUND

1. Field of the Inventions

The present invention relates in general to noise reduction in articulating connections, and more particularly, to noise reduction in articulating connections in devices for supporting a limb, including orthotic and prosthetic devices.

2. Description of the Related Art

Prosthetic devices, orthotic devices and many other mechanical parts, utilize articulated connections between members requiring motion or movement relative to each other, a user, or the surrounding environment. Common articulating connections often include a bushing, or a bore in the base material, along with a pin that extends through the bushing or bore. Articulating capability of the pin and bushing relative to each other, such as free rotation by and about the pin requires a slight clearance between a pin outer diameter and an inner surface of the bore or bushing.

Cyclical loading of the articulating connection (e.g., back-and-forth in opposing directions) results in an impact between the pin and bushing or bore, where the interacting load bearing contact surfaces of the pin and bushing lose contact with each other for a short while before reestablishing contact. Such an impact during the operation of the articulating connection results in accelerated or undesired wear of the individual interacting members and elements. Additionally, the cyclical contact between the pin and bushing or bore can generate noise during use of the articulating connection (e.g., a clicking noise). In certain device applications, such wear and/or noise is undesirable.

A conventional articulating connection 12 in a prosthetic or orthotic limb support member P is shown in FIGS. 1-3, which depict the disadvantageous features of a conventional articulating connection discussed above. The articulating connection 12 includes a load bearing pin 16, which can be removably attached to, or integral with, the limb support member P, and a bushing 18 into which the load bearing pin 16 extends. The interacting diametral features of the load bearing pin 16 and the bushing 18 are generally sized and toleranced to allow installation and assembly of the pin 16 and the bushing 18 and allow rotational movement between the load bearing pin 16 and the bushing 18.

Generally, the load bearing pin 16 has an outer diameter smaller than an inner diameter of the bushing 18 that defines a clearance E between the two different diameters that is sufficient to allow the pin 16 and the bushing 18 to easily be assembled and to articulate with respect to each other. Creating an articulating connection 12 with a small clearance increases the time and cost of manufacture of the articulating connection 12, as well as presents the likelihood of seizingly coupling the two members together and precluding all movement between the load bearing pin 16 and the bushing 18 (e.g., as the material of the pin 16 and bushing 18 expand due to heat generation during use). Articulating connections with a larger clearance can be manufactured faster and at lower cost. However, the greater the clearance, the greater the cyclical load impact and noise between the load bearing pin 16 and the bushing 18, as discussed above.

Thus, FIG. 1 depicts the typical unloaded and concentrically situated relationship between the load bearing pin 16 and the bushing 18 with a substantially similar clearance gap E all around the diameter of the load bearing pin 16. However, as depicted in FIGS. 2 and 3, during operation of the limb support member P, the coupled members disposed about the articulating connection will impart a first force on the bushing 18 and the load bearing pin 16 such that the load bearing pin is eccentrically disposed to contact the bushing 18 at a common point of surface tangency between the bushing 18 and the load bearing pin 16. Thus a first eccentric clearance E' is established between the bushing 18 and the load bearing pin 16. Upon further operational use of the prosthetic device a second substantially opposing load is imparted on the articulating connection such that a second eccentric clearance E" is established between the bushing 18 and the load bearing pin 16, where E" is substantially diametrally opposed about eccentric clearance E'. A conventional articulating connection, for example in a prosthetic or orthotic device, thus produces cyclical opposing radial impact loads on the load bearing pin 16 and the bushing 18, as well as adjacent articulating connection members of the prostheses or orthoses linkages. The cyclical impact loading impairs the wear life of the articulating connection members and produces undesirable operating noise.

Accordingly, there is a need for an improved articulating connection that solves some of the disadvantages discussed above.

SUMMARY

In accordance with one embodiment, a limb support device is provided, comprising a first support member, a second support member, and an articulating connection that pivotably couples the first support member and the second support member. The articulating connection comprises one or more articulating connection members coupled to one of the support members and one or more apertures in another of the support members configured to receive the articulating connection member therein. The articulating connection further comprises an actuation member configured to apply a force on the articulating connection member to eccentrically align the articulating connection member relative to the aperture so that the articulating connection member continuously follows and contacts a bearing surface of the aperture during use of the limb support device.

In accordance with one embodiment, a limb support device is provided, comprising a first support member, a second support member, and an articulating connection that pivotably couples the first support member and the second support member. The articulating connection comprises one or more first articulating connection members coupled to one of the support members and one or more second articulating connection members in another of the support members and configured to movably receive the first articulating connection member therein. The articulating connection further comprises an actuation member configured to apply a force on the first articulating connection member to eccentrically align the first articulating connection member relative to the second articulating connection member so that the first articulating connection member continuously follows and contacts a bearing surface of the second articulating connection member during use of the limb support device. The continuous contact thereby inhibits noise generation from the interaction of the first and second articulating connection members.

In accordance with still another embodiment, a prosthetic device is provided, comprising a first prosthetic member, a second prosthetic member, and an articulating connection that pivotably couples the first prosthetic member and the second prosthetic member. The articulating connection comprises one or more first articulating connection members coupled to one of the prosthetic members and one or more second articulating connection members coupled to another of the prosthetic members and configured to rotatably receive the first articulating connection member therein. The articulating connection further comprises an actuation member configured to apply a force on the first articulating connection member to eccentrically align the first articulating connection member relative to the second articulating connection member so that the first articulating connection member continuously follows and contacts a bearing surface of the second articulating connection member during use of the prosthetic device. The continuous contact thereby inhibits noise generation from the interaction between the second articulating connection member and the first articulating connection member.

Further features and advantages of the present invention will become apparent to those of ordinary skill in the art in view of the detailed description of preferred embodiments which follow, when considered together with the attached drawings and claims.

DETAILED DESCRIPTION OF THE PREFERRED EMBODIMENTS

In the following description of the preferred embodiments, reference is made to the accompanying drawings which form a part thereof, and in which is shown by way of illustration a specific embodiment of the invention. It is understood that other embodiments may be utilized and structural changes may be made without departing from the scope of the present invention.

Figure 1:
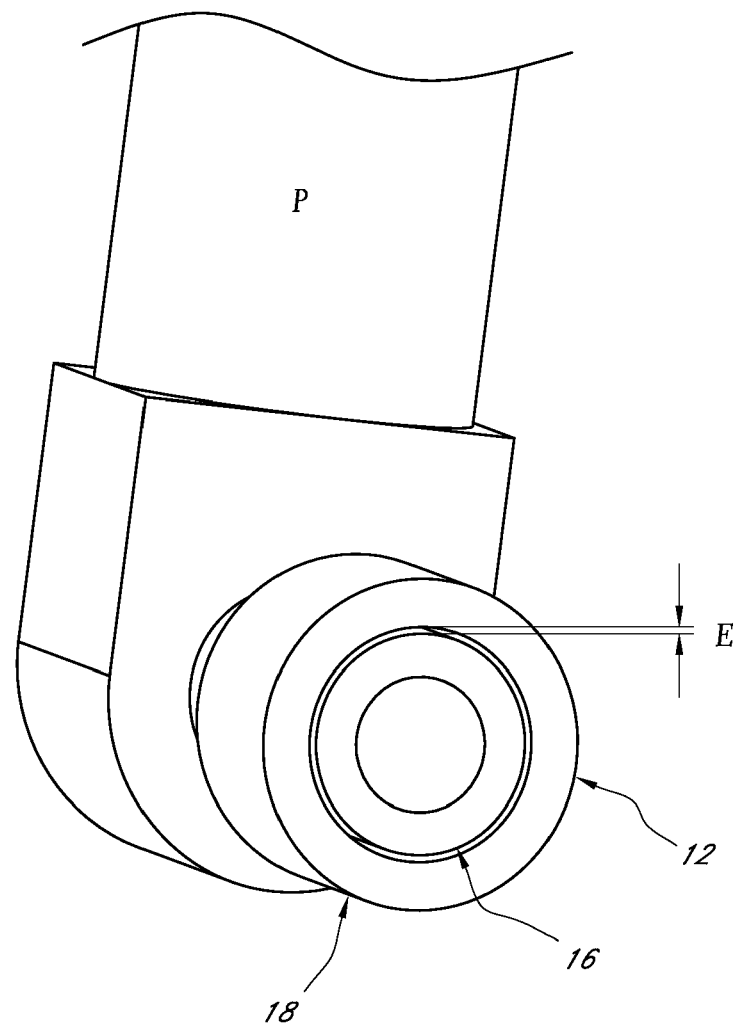
FIG. 1 is a perspective view of a conventional articulating connection in a limb support member with a load bearing pin in a first position relative to a bushing during use of the articulating connection.
Figure 2:
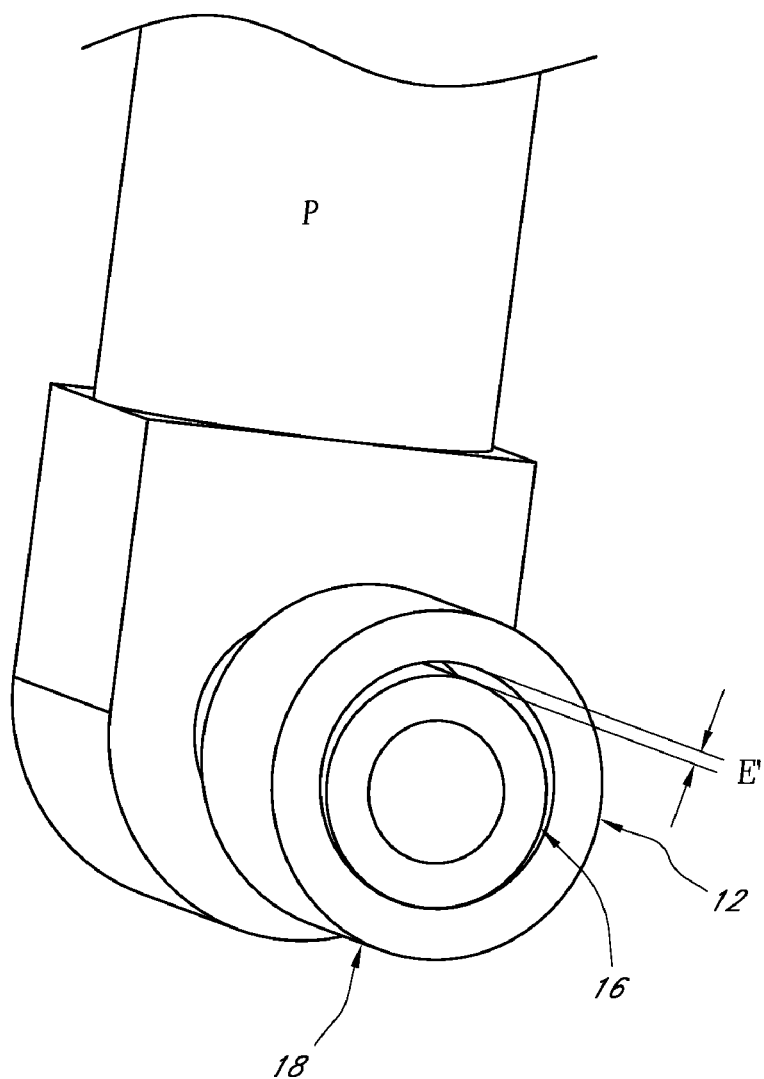
FIG. 2 is a perspective view of the conventional articulating connection of FIG. 1, with the load bearing pin in a second position relative to the bushing during use of the articulating connection.
Figure 3:
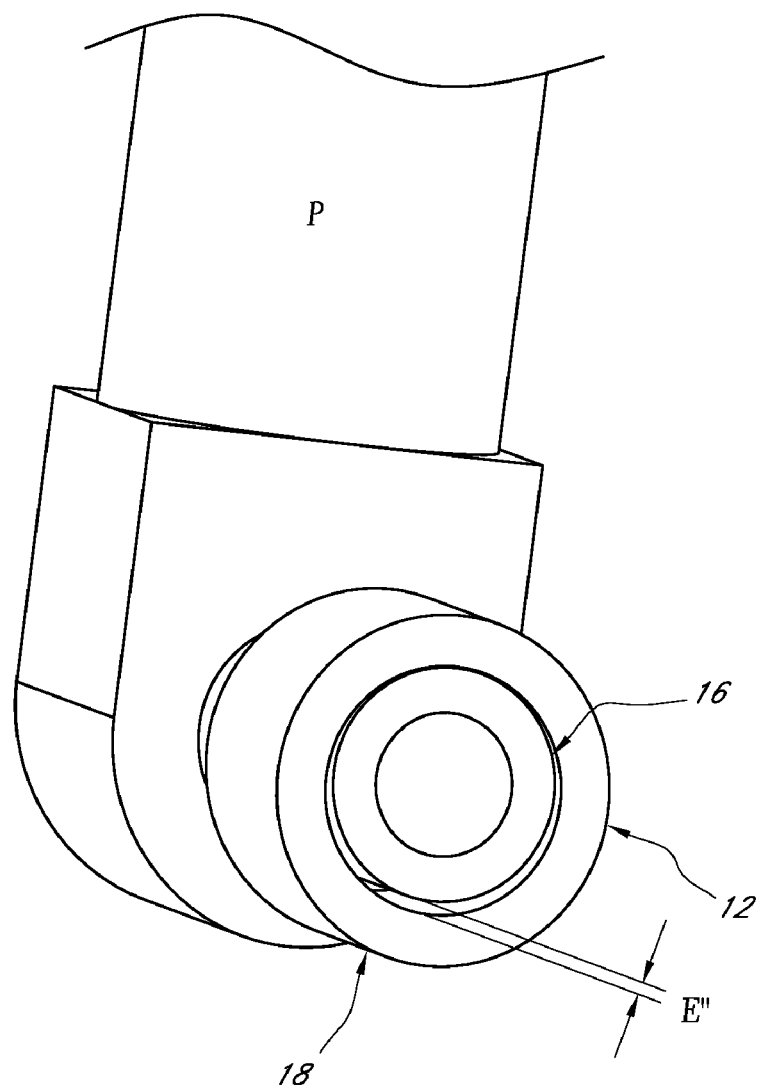
FIG. 3 is a perspective view of the conventional articulating connection of FIG. 1, with the load bearing pin in a third position relative to the bushing during use of the articulating connection.
Figure 4:
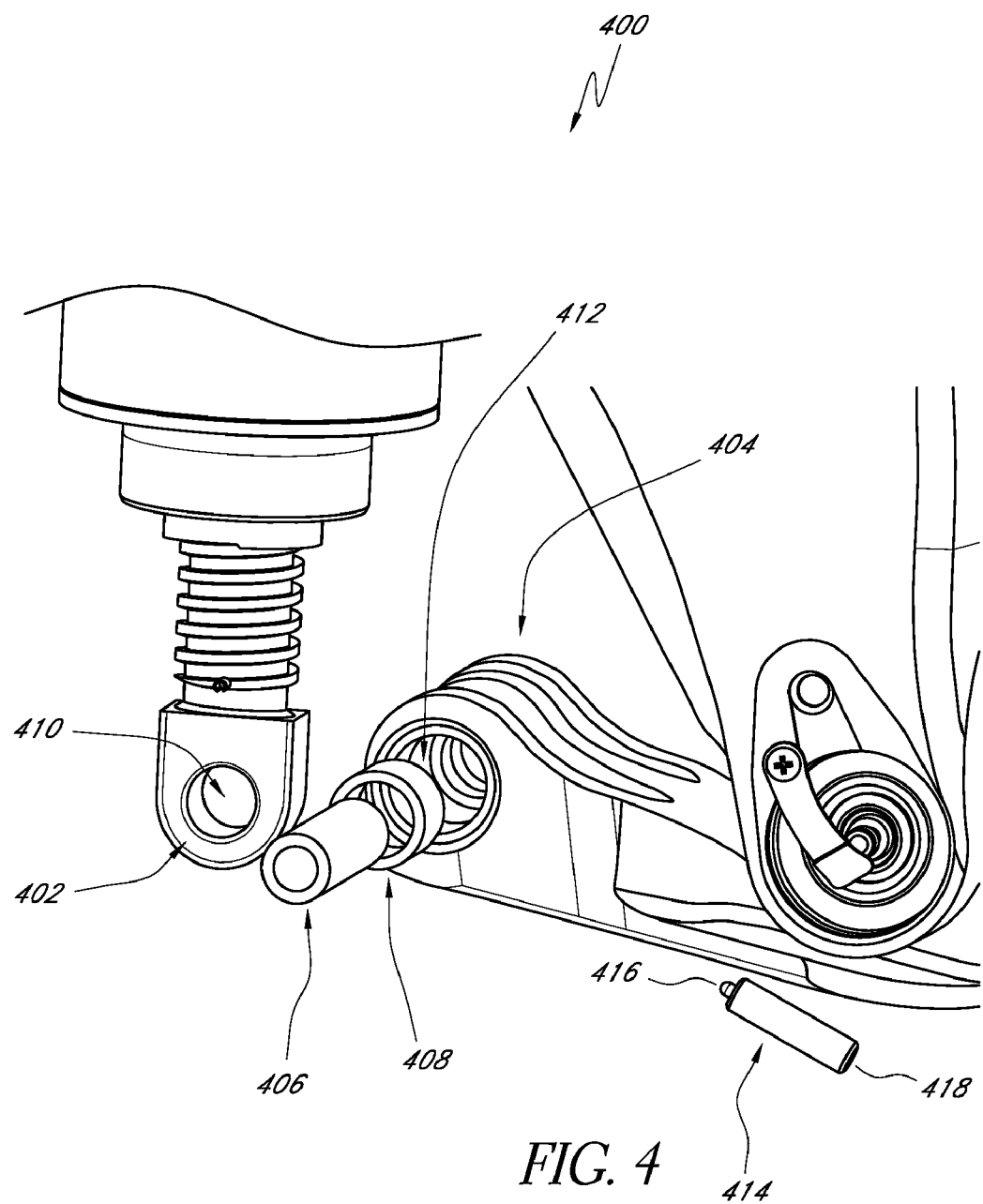
FIG. 4 is an exploded view of an embodiment of a limb support device with an articulating connection having an eccentrically located load bearing pin.
Figure 5:
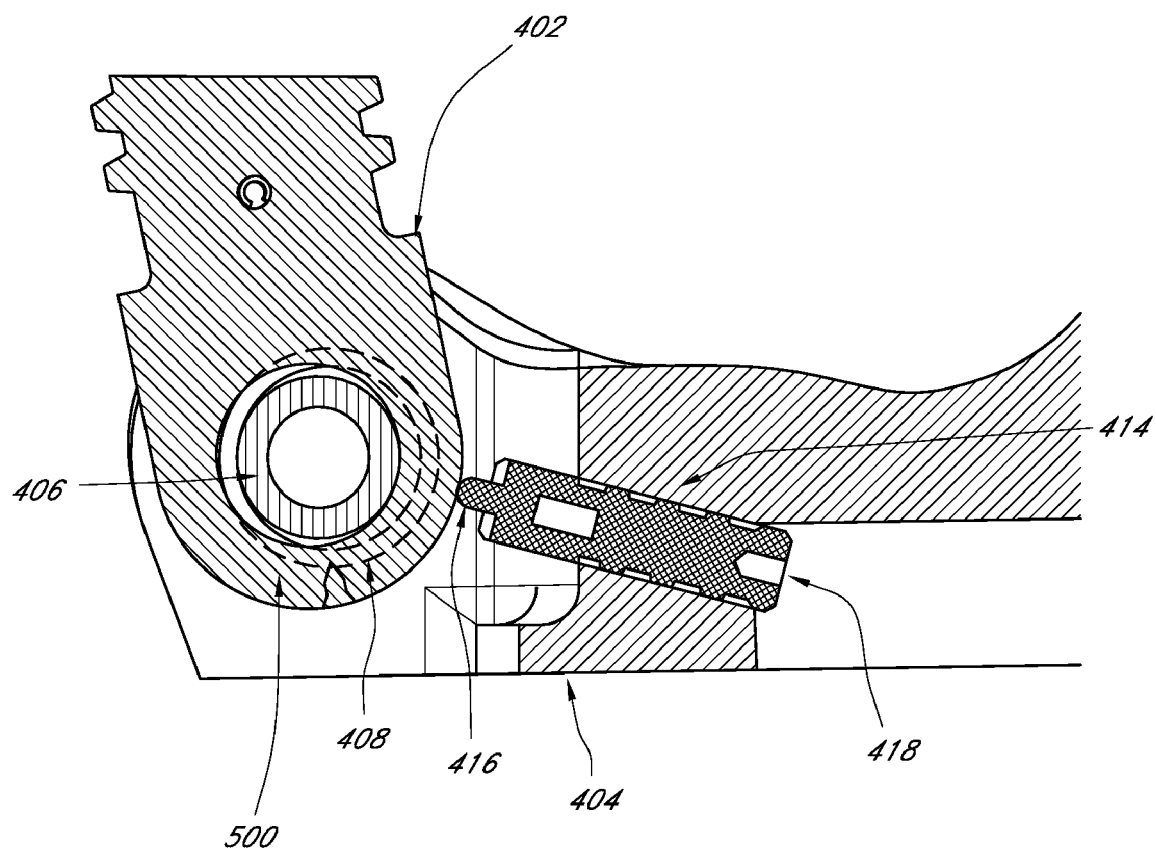
FIG. 5 is a cross section view of the prosthetic device of FIG. 4.

FIG. 4 is an exploded view of a limb support device and in particular a prosthetic device 400 having a first support member 402 and a second support member 404. In one embodiment, the first support member 402 can be an ankle actuator or connecting member in a prosthetic device and the second support member 404 can be a foot member or foot plate. The prosthetic device 400 can include an articulating connection 500, as illustrated in FIG. 5, with a first articulating connection member and a second articulating connection member. In the illustrated embodiment, the first articulating connection member is a load bearing pin 406 and the second articulating connection member is a bushing 408, that may be engagingly coupled to the first support member 402 and the second support member 404, respectively, by extension or interaction through a first aperture 410 of the first support member 402 and a second aperture 412 of the second support member 404. Prosthetic device 400 can also include an actuation member, for example a spring loaded pin 414 having a first end 416 and a second end 418 as shown in the embodiment of FIG. 5. However any suitable actuation device or equivalent can be used. In another embodiment, the first and second articulating connection members can be other suitable mechanisms. For example, the articulating connection can be a ball joint, where the first articulating connection member can be a ball joint bearing and the second articulating connection member can be a ball joint socket that pivotally couples to the ball joint bearing.

The load bearing pin 406 may be substantially cylindrical in shape, having an axial length, a substantially smooth, slidingly capable, outer surface to accommodate sliding interaction with other coupled members of the articulating connection 500, and an outer diameter sized for the appropriate intended application. In one embodiment, the load bearing pin 406 can be made of a rigid structural material, e.g. a metallic, plastic, composite, ceramic material, or the like. However, the load bearing pin 406 can be made of any suitable material. The load bearing pin 406 may also be hollow or solid according to the desired application.

The bushing 408 may be a ring shaped member having an inner diametral bearing surface and an outer diametral bearing surface, where the outer diameter feature is sufficiently larger than the inner diameter feature to meet the application design needs, e.g. of the prosthetic device. The inner diameter feature of the bushing 408 is larger than the diameter of the load bearing pin 406 such that the load bearing pin 406 may freely pass through and locally engage, at a common point of tangency, the inner diameter of the bushing 408.

The first support member 402 has aperture 410 that may be sized sufficiently large enough to accept the outer diameter of the bushing 408. Alternatively, if the bushing 408 is comprised of multiple separate elements situated only within the aperture 412 of the second support member 404, where the aperture 410 is a bearing surface, aperture 410 may be sized to accept the smaller outer diameter load bearing pin 406.

In one embodiment, the spring loaded pin 414 may have a cylindrical shape. However, in other embodiments, the spring loaded pin 414 can have any other suitable shape for use with the prosthetic device 400. The spring loaded pin 414 preferably extends along an axis from the first end 416 to the second end 418.

Figure 6:
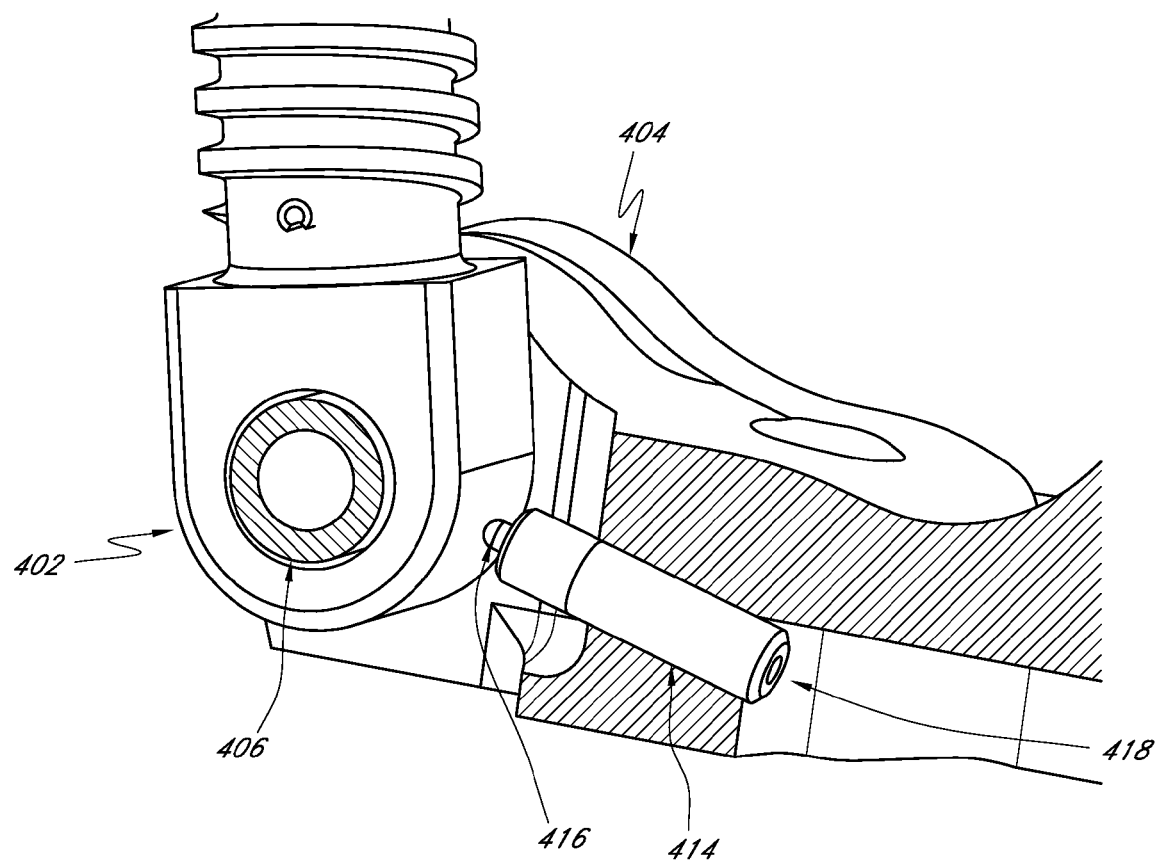
FIG. 6 is a perspective cross section view of the articulating connection of FIG. 4.
Figure 7:
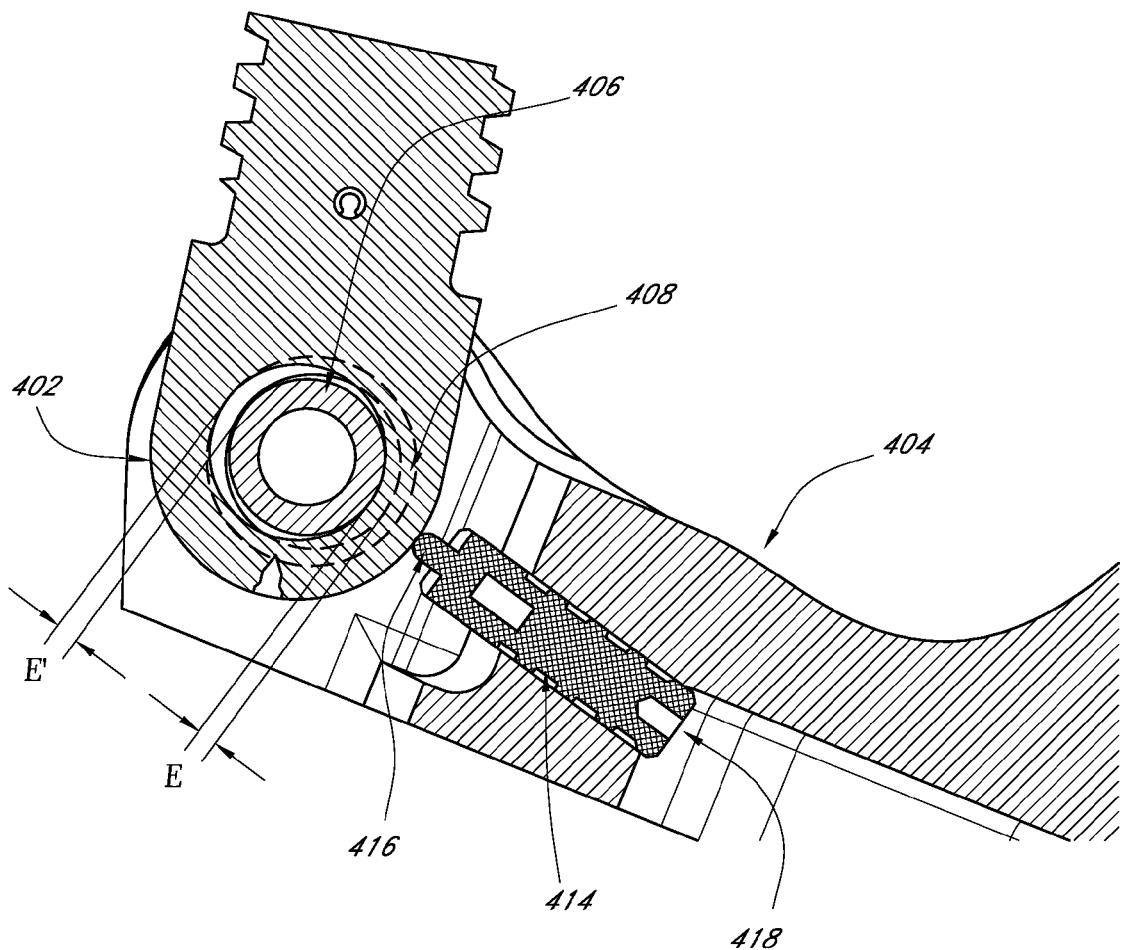
FIG. 7 is a cross section view of the prosthetic device of FIG. 4.

FIGS. 5-7 are cross-sectional views of the limb support device 400 depicting the assembled interaction of an embodiment of the first support member 402, the second support member 404, the load bearing pin 406, the bushing 408, and the spring loaded pin 414.

In the illustrated embodiment, the spring loaded pin 414 may be disposed in a recess of the second support member 404 such that the first end 416 is generally in contact with an outer surface of the first support member 402 and the second end 418 is generally coupled to the second support member 404.

The spring loaded pin 414 may include a spring mechanism capable of imparting a preload at the first end 416 and the second end 418 when the prosthetic device is in a first nominally loaded condition. In one embodiment, a spring can be disposed about the body of the pin 414. In another embodiment, a spring can be disposed within the body of the pin 414, proximate the second end 418, where the spring is configured to apply a force on and actuate the first end portion 416 into contact with the first support member 402. In still another embodiment, the spring can be disposed between the second end 418 of the spring-loaded pin 414 and the recess in the second support member 404. However, the spring loaded pin 414 can have other suitable configurations. The spring can include any suitable spring mechanism, e.g. helical coil, leaf, torsional, or the like. The spring can be preloaded in compression or tension such that the first support member 402 and the second support member 404 are forcibly drawn together or pushed away from each other, as the case may be, in a general direction of the axis of the spring loaded pin 414.

The spring loaded pin 414 may be fabricated from a variety of materials, e.g. metallic, plastic, composite, or the like. The spring loaded pin may be made of either a harder, softer or similar material than the first support member 402 and the second support member 404, as dictated by the desired wear pattern of the limb support device 400 assembly.

In other embodiments, the spring loaded pin may be coupled between the first support member 402 and the second support member 404 in a variety of directions as may be advantageous to the structural geometry of both members without affecting the advantageous features outlined below. The coupling of spring loaded pin 414 to the first and/or the second support members 402, 404 may be accomplished by a variety of methods, e.g. fasteners (such as bolts or screws), welded, integrally molded, or integrally threaded in a fastener type fashion. The spring constant of the spring of the spring loaded pin 414 may vary across a wide range to impart a variety of forces established by the desired prosthetic or orthotic device 400 function for rigidity, wear, size of the user, comfort to the user, geometric limitations of the first and the second support members 402, 404, or the like. Likewise, physical geometry of the spring loaded pin may vary in length, width, diameter, and the like, in accordance with prosthetic device 400 design requirements. In another embodiment, the user may be able to modify the physical orientation and/or the spring constant of the spring loaded pin 414 for a particular purpose or application (e.g., the spring tension or compression can be adjustable in one embodiment, such as by varying the location of a fastener attached to the spring).

The installed spring loaded pin 414 advantageously establishes a preloaded condition on the articulating connection 500, creating variation in the concentricity, or eccentricity, between the first support member aperture 410, the second support member aperture 412, the load bearing pin 406 inner and outer diameter surfaces, and the bushing 408 inner and outer diameter surfaces. Specifically, the spring loaded pin 414 can exert a force on the first support member 402, which can in turn exert a force on the load bearing pin 406. The preload resultant force preferably eccentrically aligns the load bearing pin 406 and the bushing 408 to force the bushing 408 and the load bearing pin 406 to contact each other at a common area of tangency throughout the operation of the limb support device 400. The preload resultant force therefore causes the load bearing pin 406 to continuously follow and contact the bearing surface of the bushing 408. As shown in FIG. 7, the spring loaded pin urges the right-hand side of the first support member 402 against the load bearing pin 406, creating a gap eccentricity E' on the left hand side between the load bearing pin 406 and the first support member 402. Correspondingly, the spring loaded pin 414 urges the left-hand side of the load bearing pin 406 against the bushing 408, creating a gap eccentricity E on the right hand side between the load bearing pin 406 and the bushing 408. Thus, the spring loaded pin 414 exerts a perpendicular force on the load bearing pin 406 via the first support member 402 to maintain the load bearing pin 406 in substantially continuous contact with the bushing 408.

Such a pre-loaded offset feature between load bearing pin 406 and bushing 408 advantageously mitigates the effects of the cyclical compression or tension load induced impact between the load bearing pin 406 and the bushing 408 due to clearance induced "play" between load bearing pin 406 and bushing 408. The continuous contact inhibits impact loading as contact between load bearing pin 406 and bushing 408 continually exists due to the preload of spring loaded pin 414 urging the pre-existing contact, thereby reducing noise generation and wear during use of the articulating connection 500.

The continuous contact inhibits impact loading due to the operational use loads, including loads in substantially the same direction as the spring loaded pin force and all other directional loads. First, as noted above, loads in substantially the same direction as the spring loaded pin 414 will not result in significant impact because contact already exists between the load bearing pin 406 and the bushing 408 in the direction that user operation imparts a force on the articulating connection 500. In one embodiment, the spring loaded pin 414 may function as a damper, so that any resulting impact between the load bearing pin 406 and the bushing 408 is less than if there were no spring loaded pin 414 imparting a force on the articulating connection 500. In another embodiment, the spring constant of the spring loaded pin 414 may be of a sufficient magnitude to preclude the operational load of limb support device 400 from imparting a force of sufficient magnitude on the articulating connection 500 to move or relocate load bearing pin 406 away from contact with the bushing 408.

As can be seen by the present disclosure, the limb support device 400 articulating connection 500 provides several advantageous features. The continuous pre-established contact inhibits noise generation and increases wear life of the pin 406, bushing 408 and the articulating connection or joint assembly 500. Additionally, the spring loaded pin 414 allows increased clearance between the load bearing pin 406 and bushing 408 upon assembly, and therefore greater design and manufacturing flexibility in providing tolerances for these elements, reduces friction between elements of the articulating connection 500, and reduces or eliminates mismatch and stresses of articulating connections that are not pre-loaded to an eccentric position. Though the embodiment illustrated in FIGS. 4-7 depict an articulating connection or joint 500 in a prosthetic device 400, one of ordinary skill will recognize that the articulating connection 500 with the spring-loaded pin 414 can be incorporated in an orthotic device, such as, but not limited to, a knee, elbow or ankle brace.

Figure 8:
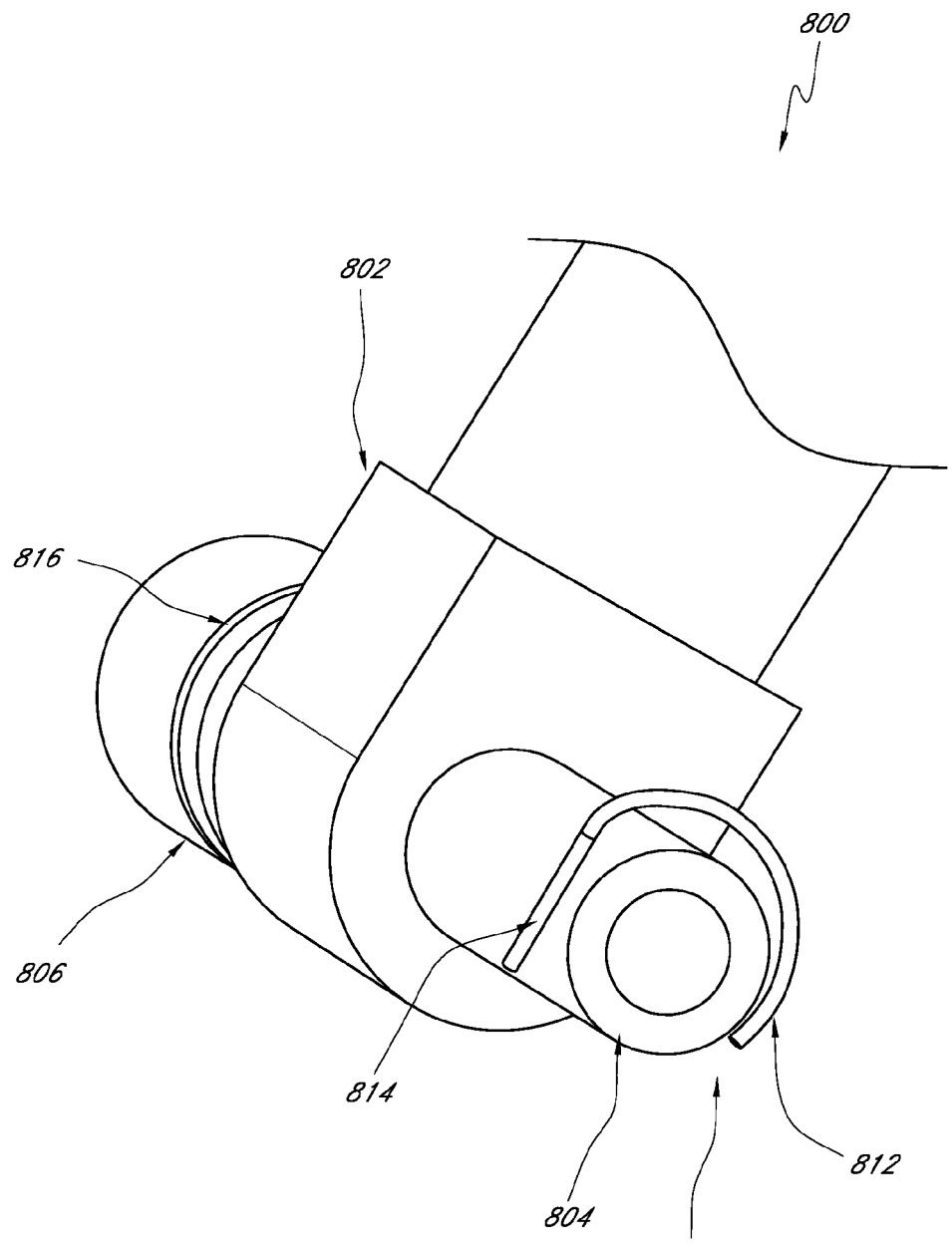
FIG. 8 is a perspective view of another embodiment of an articulating connection in a limb support device.
Figure 9:
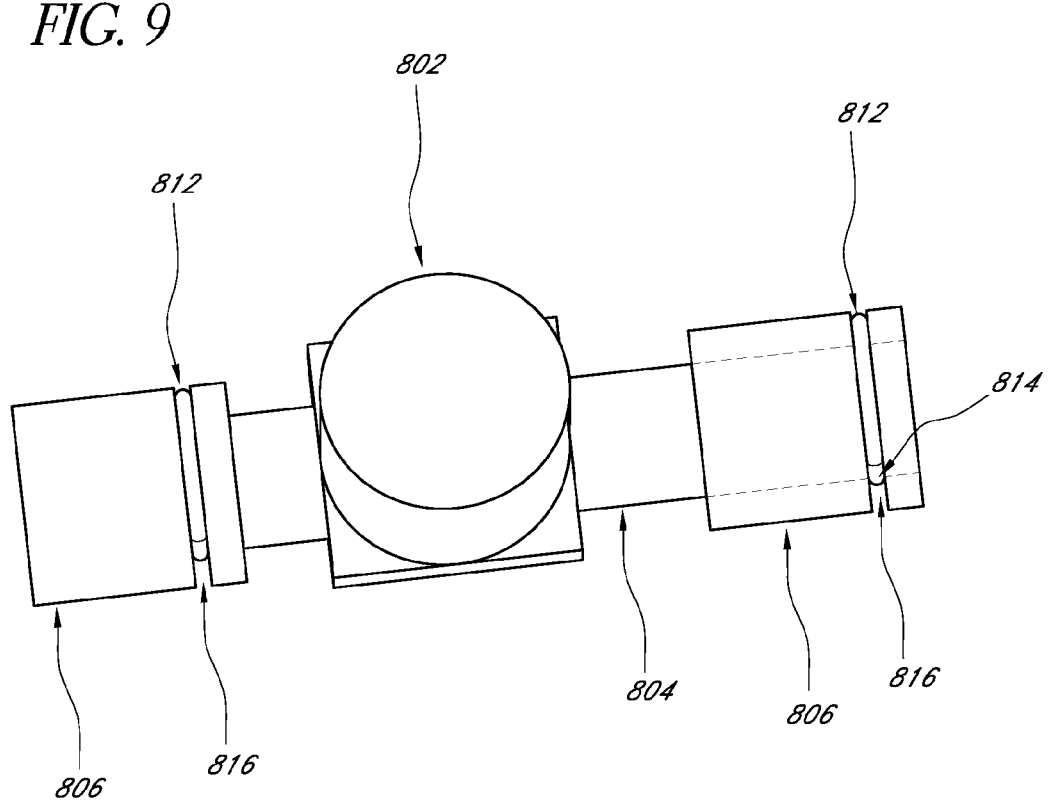
FIG. 9 is a top view of the articulating connection of FIG. 8.
Figure 10:
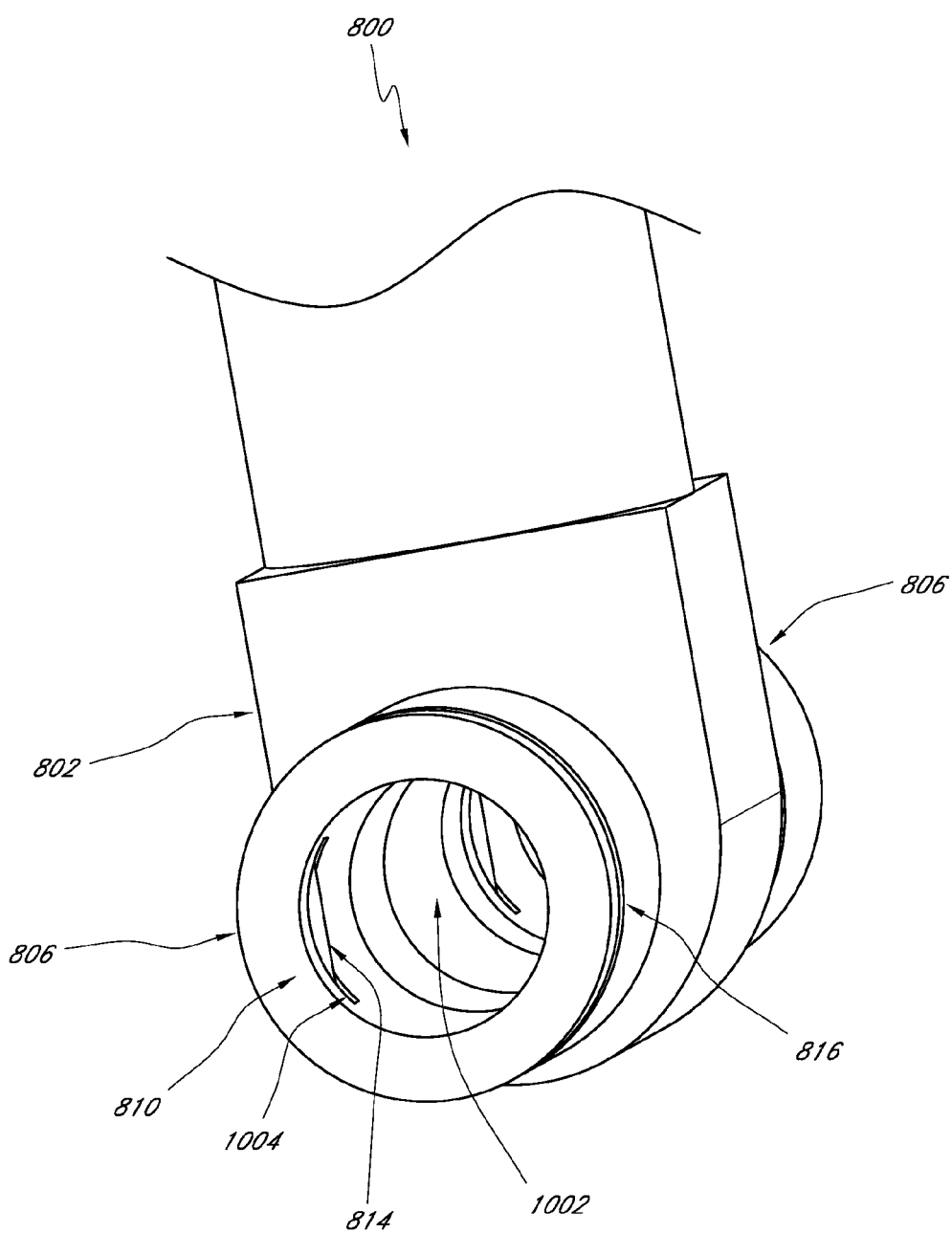
FIG. 10 is a perspective view of the articulating connection of FIG. 8.

FIGS. 8-10 depict another embodiment of a limb support device 800 with a first support member 802 and an articulating connection 810. The articulating connection 810 can include a first articulating connection member, or load bearing pin 804, and a second articulating connection member, or a bushing 806, on each side, or alternatively a single side, of the first support member 802. The load bearing pin 804 can be removably attached or integral to the first support member 802. The load bearing pin 804 can be received into the first aperture 1002 of bushing 806 to establish articulating connection 810. The articulating connection 810 can further include at least one actuation member, or spring member 812, disposed about at least a portion of a load bearing pin 804 and at least a portion of the bushing 806. The spring member 812 is shown in FIG. 8 without the corresponding bushing on the front side to allow the depiction of the spring member 812. The spring member 812 preferably imparts a force on the load bearing pin 804 and establishes a continuous pre-load point of surface contact at a shared tangency between the outer diameter of the load bearing pin 804 and the inner diameter of the bushing 806 during the use of the limb support device 800, including before the limb support device 800 is loaded under the operational weight of the user. The preload resultant force applied by the spring 812 causes the load bearing pin 804 to continuously contact and follow the bearing surface of the bushing 806. Thus, the preload resultant force applied by the spring 812 eccentrically aligns the load bearing pin 804 and bushing 806 by way of the continuous perpendicular loaded contact so that the load bearing pin 804 can be in substantially continuous contact with a bearing surface of the bushing 806.

In the illustrated embodiment of FIGS. 8-10, the spring member 812 can be disposed about, and make contact with, both the bushing 806 and the load bearing pin 804 by making at least partial contact with an outer surface of the bushing 806 as well as at least partial contact with an outer surface of the load bearing pin 804 in substantially the same planar location, such plane extending generally normal to the axis of the load bearing pin 804 and the bushing 806. In another embodiment, the spring 812 can be shaped so as to contact the load bearing pin 804 and bushing 806 at different planar locations. In the illustrated embodiment, the spring 812 can be disposed in a recess or slot 816 formed in the outer surface of the bushing 806 that, in one embodiment, can extend circumferentially 360 degrees around the bushing 806. The slot 816 can be sufficiently sized to accept the spring 812. In the illustrated embodiment of FIG. 10, where the load bearing pin 804 is not shown for clarity, a portion of the slot 816 locally extends radially through the thickness of the bushing 806 and creating a second aperture 1004, so that at least a portion of the spring 812 can extend through the slot 816 and contact the outer surface of the load bearing pin 804.

In one embodiment, the spring member 812 is generally a circular or semicircular ring spring that further may include an eccentric member 814 to create a continuous perpendicularly loaded contact between the pin 804 and the bushing 806. However, the spring member 812 can have other suitable shapes. Likewise, eccentric member 814 may be any shape sufficient to rest in the slot 816, project through the second aperture 1004, and exert a force on the load bearing pin 804.

As shown in the illustrated embodiment of FIG. 10, spring 812 can resiliently dispose eccentric member 814 toward the load bearing pin 804. Direct contact between spring 812 eccentric member 814 and the load bearing pin 804, through the second aperture 1004 located in slot 816, can impart a force on the load bearing pin 804 to urge the load bearing pin 804 toward contact with the bushing 806 at a location opposite the eccentric member 814. Direct contact between the eccentric member 814 and the load bearing pin 804 is achieved by way of the second aperture 1004 in the slot 816, configured to allow at least a portion of the eccentric element 814 to extend through the second aperture 1004 while retained in the slot 816 on an outer diameter surface of the bushing 806.

The springing, or actuation, driven contact of the eccentric member 814 with the load bearing pin 804 advantageously imparts a continuous eccentric inducing load on the load bearing pin 804 to urge the load bearing pin 804 into substantially continuous contact with the bushing 806 inner diameter surface. The direction of imparting force on the load bearing pin 804 and the bushing 806 is determined by the diametral location of the second aperture 1004. The direction of eccentric imparting force would be substantially diametrally opposite the location of the second aperture 1004 in the slot 816 disposed around the bushing 806.

As shown in FIGS. 8 and 9, more than one bushing 806 may interact with the load bearing pin 804. In such case, as more than one bushing 806 is required to form articulating connection 810, then the corresponding number of spring members 812 and slots 816 and second apertures 1004 may exist for each of the individual bushing 806 members to be coupled to articulating connection 810. In another embodiment, more than one spring member 812 can be disposed in corresponding slots 816 (e.g. the same slot or different slots) on the bushing 806 so that the spring members 812 can exert a force on the load bearing pin 804 at multiple axial and/or circumferential locations to effect continuous contact between the load bearing pin 804 and the bushing 806. Alternatively, an actuation member, or spring 812, can have more than one eccentric member 814 to contact a load bearing pin 804 at more than one location or point.

Common articulating connections, of the type disclosed in the embodiments above, can be implemented on prosthetic or orthotic devices requiring a form of movement or motion, for instance rotational interaction, between members of the device. More particularly, the articulating connection for an orthotic device can be implemented, for example, in a knee, elbow, wrist, shoulder or ankle brace, though the articulating connection can be used in other orthotic devices. Similarly, the articulating connection for a prosthetic device may be implemented on a foot prosthetic, e.g. as an ankle joint, or on a knee prosthetic, e.g. as a knee joint.

Further details on devices that can incorporate the embodiments of the articulating connection or joint disclosed herein can be found in U.S. application Ser. No. 11/056,344, filed on Feb. 11, 2005, now U.S. Pub. No. 2005-0197717; U.S. application Ser. No. 11/219,317, filed Sep. 1, 2005, now U.S. Pub. No. 2007-0156252; U.S. application Ser. No. 07/743,583, filed on Aug. 9, 1991, now U.S. Pat. No. 5,092,902; U.S. application Ser. No. 08/176,645, filed Dec. 30, 1993, now U.S. Pat. No. 5,443,521; U.S. application Ser. No. 08/883,614, filed Jun. 26, 1997, now U.S. Pat. No. 5,888,212; and U.S. application Ser. No. 09/767,367, filed Jan. 22, 2001, now U.S. Pat. No. 6,764,520, the entire contents of all of which are hereby incorporated by reference in their entirety and should be considered a part of this specification.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. For example, the embodiments disclosed above can be used with articulating connections or joints in orthotic devices as well as prosthetic devices. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A prosthetic device, comprising:
    a prosthetic component disposed at least partially at a location corresponding to a location of a natural human ankle;
    a prosthetic foot member; and
    an articulating connection that pivotably couples the prosthetic component and prosthetic foot member, the articulating connection comprising:
        one or more first articulating connection members coupled to the prosthetic component,
        one or more second articulating connection members in the foot member and configured to movably receive the first articulating connection member therein, and
        an actuation member disposed at least partially within a recess of the prosthetic foot member and configured to move in unison with the foot member relative to the prosthetic component, the actuation member configured to apply a force on the first articulating connection member to eccentrically align the first articulating connection member relative to the second articulating connection member so that the first articulating connection member continuously follows and contacts a bearing surface of the second articulating connection member during use of the prosthetic device, thereby inhibiting noise generation from the interaction of the first and second articulating connection members.

2. The prosthetic device of claim 1, wherein the first articulating connection member is a load-bearing pin.

3. The prosthetic device of claim 1, wherein the second articulating connection member is a bushing coupled to said foot member.

4. A prosthetic device, comprising:
    an actuator for a prosthetic ankle;
    a prosthetic foot member; and
    an articulating connection that pivotably couples the actuator and prosthetic foot member, the articulating connection comprising:
        one or more load-bearing pins coupled to one of the actuator and foot member,
        one or more apertures in another of the actuator and foot member and configured to rotatingly receive the load-bearing pin therein, and
        an actuation member disposed at least partially within the prosthetic foot member, the actuation member configured to apply a force on the load-bearing pin to eccentrically align the load-bearing pin relative to the aperture so that the load-bearing pin is urged to substantially continuously follow and contact a bearing surface of the aperture during use of the prosthetic device, thereby inhibiting noise generation from the interaction of the aperture and load-bearing pin.

5. The prosthetic device of claim 4, wherein the aperture is defined by a bushing coupled to said another of the actuator and foot member.

6. The prosthetic device of claim 5, wherein the actuation member is a spring member having a first portion that contacts an outer surface of the bushing and a second portion that contacts an outer surface of the load-bearing pin.

7. The prosthetic device of claim 5, wherein the actuation member is a spring-loaded pin member disposed outside the bushing, the spring-loaded pin member configured to apply a force on the load-bearing pin to eccentrically align the load-bearing pin relative to the bushing.

8. The prosthetic device of claim 4, wherein the actuation member comprises a first portion that contacts the actuator and a second portion that contacts the foot member, the actuation member applying a force on the actuator and foot member to apply a force on the load-bearing pin.

9. A prosthetic device, comprising:
    an actuator for a prosthetic ankle;
    a prosthetic foot member; and
    an articulating connection that pivotably couples the actuator and foot member, the articulating connection comprising:
        one or more first articulating connection member coupled to one of the actuator and foot member,
        one or more second articulating connection member coupled to another of the actuator and foot member and configured to rotatingly receive the first articulating connection member therein, and
        an actuation member disposed at least partially within the prosthetic foot member, but disposed at least partially outside the second articulating connection member, the actuation member configured to apply a force on the first articulating connection member to eccentrically align the first articulating connection member relative to the second articulating connection member so that the first articulating connection member continuously follows and contacts a bearing surface of the second articulating connection member during use of the prosthetic device, thereby inhibiting noise generation from the interaction between the second articulating connection member and first articulating connection member.

10. The prosthetic device of claim 9, wherein the actuation member is a spring-loaded pin member.

11. The prosthetic device of claim 9, wherein the actuation member comprises a first portion that contacts the actuator and a second portion that contacts the foot member, the actuation member applying a force on the actuator and foot member to apply a force on the first and/or second articulating connection member.

12. The prosthetic device of claim 9, wherein the actuation member is configured to contact an outer surface of the first articulating connection member and an outer surface of the second articulating connection member, the actuation member exerting a force on the first and second articulating connection members to eccentrically align the first and second articulating connection members so that the first articulating connection member continuously follows and contacts the bearing surface of the second articulating connection member.

13. The prosthetic device of claim 9, wherein the articulating connection comprises two second articulating connection members and the actuation member is configured to apply a force on the first articulating connection member to eccentrically align the first articulating connection member relative to the actuator so that first articulating connection member contacts the actuator and eccentrically align the first articulating connection member relative to the second articulating connection members so that the first articulating connection member continuously follows and contacts a bearing surface of the second articulating connection members during use of the prosthetic device.

14. The prosthetic device of claim 13, wherein the two second articulating connection members comprise two bushings.

15. The prosthetic device of claim 9, wherein the actuation member moves in unison with the prosthetic foot member relative to actuator in use.

* * * * *